United States Patent [19]
Solar

[11] Patent Number: 5,403,341
[45] Date of Patent: Apr. 4, 1995

[54] PARALLEL FLOW ENDOVASCULAR STENT AND DEPLOYMENT APPARATUS THEREFORE

[76] Inventor: Ronald J. Solar, 12495 Figtree St., San Diego, Calif. 92131

[21] Appl. No.: 185,549

[22] Filed: Jan. 24, 1994

[51] Int. Cl.⁶ ............................................. A61M 29/00
[52] U.S. Cl. ......................................... 606/198; 623/1
[58] Field of Search ............... 606/108, 153, 191, 195, 606/198, 200; 623/1, 11, 12

[56] References Cited

U.S. PATENT DOCUMENTS

| | | | |
|---|---|---|---|
| 4,580,568 | 4/1986 | Gianturco | 606/198 |
| 4,950,227 | 8/1990 | Savin et al. | 623/1 |
| 5,035,706 | 7/1991 | Giantureo et al. | 606/198 |
| 5,108,416 | 4/1992 | Ryan et al. | 623/1 |
| 5,135,536 | 8/1992 | Hillstead | 606/195 |
| 5,282,824 | 2/1994 | Gianturco | 606/191 |
| 5,292,331 | 3/1994 | Boneau | 623/1 |

Primary Examiner—Stephen C. Pellegrino
Assistant Examiner—William W. Lewis
Attorney, Agent, or Firm—Stetina Brunda & Buyan

[57] ABSTRACT

A pressure expandable stent device having a first internal diameter and subsequently expandable to a second internal diameter. The stent device comprises an elongate wire member having first and second ends and a multiplicity of radius bends formed at spaced locations formed along the length thereof. Each of the bends forms an angle of approximately 180° so as to define therebetween multiple straight segments of the wire members which are disposed in generally parallel, convoluted relation to one another. The first and second ends of the wire members are positioned in co-axial alignment and fused to one another. The fusing of the first and second ends of the wire member to each other causes the straight segments to assume a cylindrical array about a longitudinal axis which defines an internal flow channel of the first internal diameter therewithin. The stent device is radially expandable to a configuration where the internal flow channel is of the second internal diameter.

54 Claims, 3 Drawing Sheets

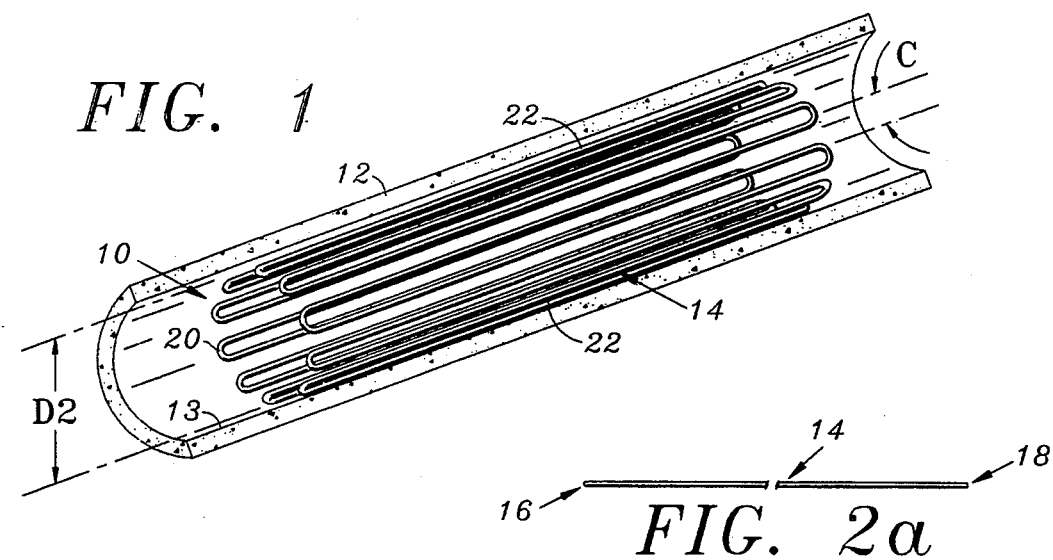
FIG. 1
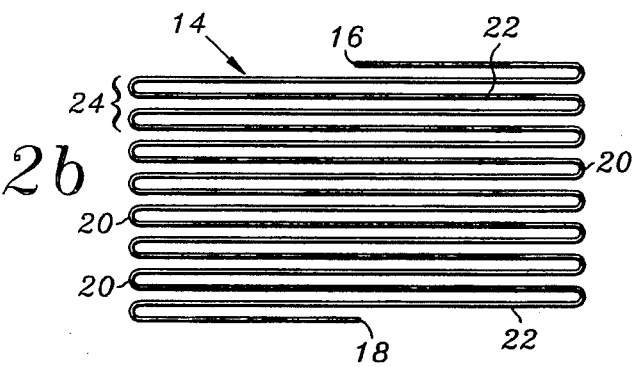
FIG. 2a
FIG. 2b
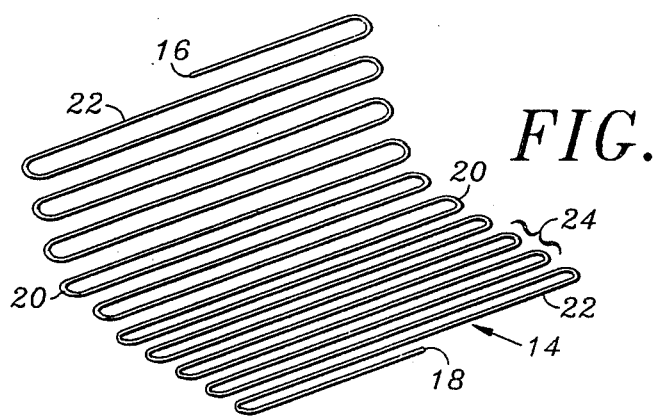
FIG. 2c
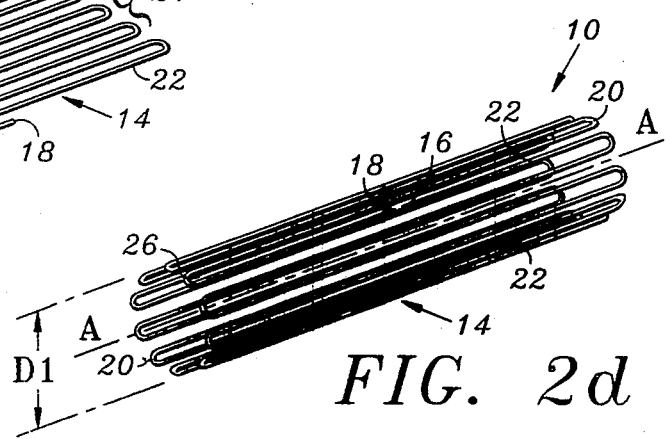
FIG. 2d

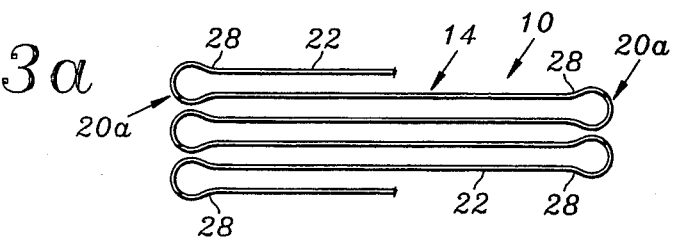
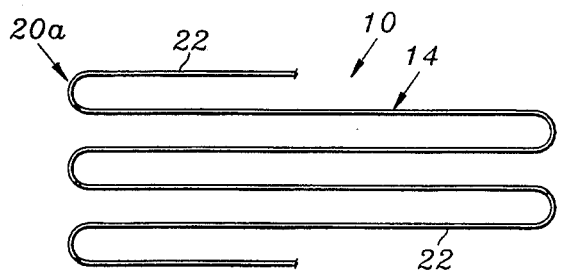
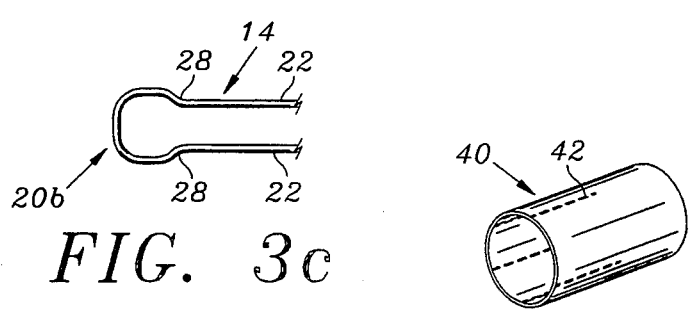
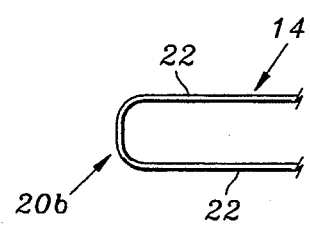
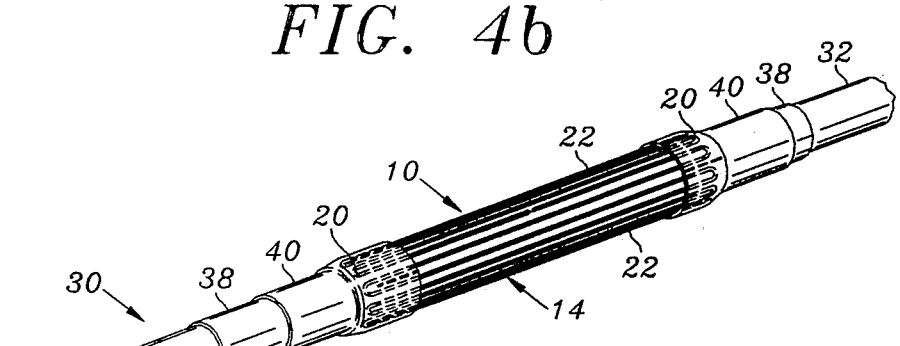
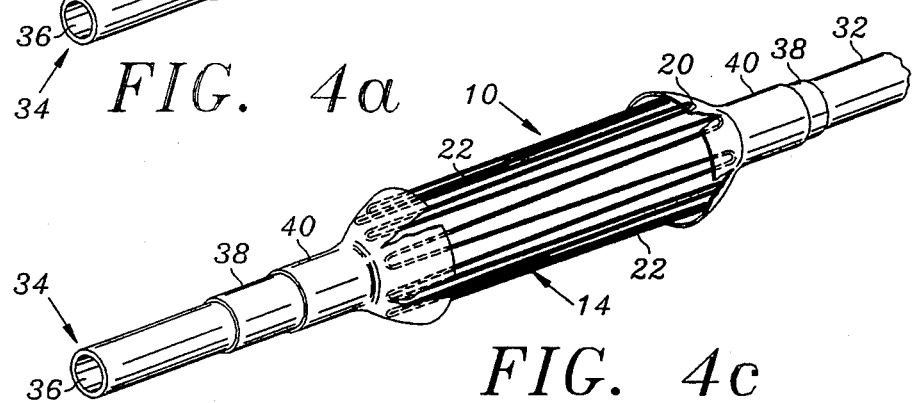

PARALLEL FLOW ENDOVASCULAR STENT AND DEPLOYMENT APPARATUS THEREFORE

FIELD OF THE INVENTION

The present invention pertains generally to medical equipment, and more particularly to endoprosthetic stent devices and apparatus for deploying the same.

BACKGROUND OF THE INVENTION

Endoprosthetic devices commonly referred to as a "stents" generally comprise a rigid structural member which may be implanted within an anatomical structure to reinforce or support a portion of the anatomical structure which has become occluded, weakened, compressed or otherwise affected by pathology. Stent devices of various configuration have heretofore been successfully utilized to reinforce or dilate numerous types of anatomical structures, including blood vessels, urogenital passageways and bile ducts.

In cardiovascular applications, endovascular stents are typically inserted into a blood vessel to dilate areas of the vessel which have become occluded by atherosclerotic plaque or constricted by an adjacent tumor. Insertion and endovascular deployment of the stent may be accomplished either intraoperatively through an open incision or percutaneously through a transluminally positioned catheter or similar introducer apparatus.

Endovascular stents of the prior art have typically fallen into two general categories of construction. The first category of endovascular stent is the self-expanding stent formed of spring metal or similar material and deployable through the lumen of a tubular catheter or sleeve such that, when the self-expanding stent is advanced out of the distal end of the catheter or sleeve, it will automatically expand so as to exert pressure against the surrounding blood vessel wall. The second category of stent is the pressure-expandable stent. Pressure-expandable stents are typically formed of rigid, pre-set material and may be deployed on an inflatable balloon or other expanding member such that, upon inflation of the balloon or expansion of the deployer, the stent will be radially enlarged to a desired diameter such that the stent becomes positioned against the surrounding blood vessel wall.

Self-expanding endovascular stents of the prior art include those described in U.S. Pat. Nos. 4,580,568 (GIANTURCO); and 4,830,003, (WOLFF, et al.) and foreign patent publication no. EP 183372A.

Pressure-expandable endovascular stents of the prior art include those described in U.S. Pat. Nos. 5,135,336 (HULSTEAD); 4,733,685 (PALMANTZ); 4,922,905 (STRECKER); 4,950,227 (SAVIN, et al.); 5,041,126 (GIANTURCO); 5,108,416 (RYAN, et al.) 5,161,547 (TOWER) (and foreign patent publications nos. EP-378151A; and EP246998A.

In clinical practice, the utilization of endovascular stent devices has generally been associated with an incidence of thromboembolic complications. Such thromboembolic complications are believed to result, at least in part, due to a) disruption of laminar blood flow by the stent itself and/or b) non-biocompatibility of the stent material.

In view of the clinical incidence of thromboembolic complications experienced with endovascular stent devices of the prior art, there remains a need for newly designed endovascular stent devices which promote non-turbulent laminar blood flow through the lumen of the blood vessel and which minimize the surface area of stent-host interface so as to minimize potential complications due to non-biocompatibility of the stent.

SUMMARY OF THE INVENTION

In accordance with a preferred embodiment of the present invention, there is provided a pressure expandable stent device which has a first internal diameter (D1) and is subsequently expandable to a second internal diameter (D2). The stent device generally comprises an elongate wire member having first and second ends. Formed at spaced locations along the wire member are a multiplicity of radius bends, each of which form an angle of approximately 180° thus defining therebetween multiple straight segments of the wire member which are disposed in generally parallel, convoluted relation to one another. The first and second ends of the wire are positioned in co-axial alignment and fused to one another, thus causing the straight segments of the wire to assume a cylindrical array about a longitudinal axis and define therewithin an internal flow channel of the first diameter (D1). The stent device is then radially expandable to a configuration whereat the internal flow channel is of the second internal diameter (D2).

In the preferred embodiment, the angle defined between any pair of the straight segments which are disposed in side-by-side relation and separated by one of the radius bends does not exceed 45°, and preferably does not exceed 30°. Additionally, the wire member is preferably fabricated from a titanium alloy, with the first and second ends of the wire being attached to each other via a weld.

Each of the radius bends may be formed having an enlarged, bulbous configuration, with the wire used to form the stent device being formed to include weakened portions which are defined between each of the enlarged bends and the pair of straight segments separated thereby. The bulbous ends and the weakened portions are adapted to maintain the straight segments in substantially parallel relation when the stent device is expanded from the first internal diameter to the second internal diameter. As an alternative to forming the bends with a bulbous configuration, each of the bends may be formed with an enlarged, generally key-shaped configuration which, together with the weakened portions of the wire, maintain the straight segments in substantially parallel relation to each other subsequent to the radial expansion of the stent device.

The stent device constructed in accordance with the present invention is preferably used in combination with a balloon catheter comprising a catheter body, an inflatable balloon positioned upon the catheter body and an inflation lumen defined within the catheter body for selectively inflating and deflating the balloon. The stent device is extended over the catheter body to a position whereat the balloon is disposed within the flow channel, with the stent device being radially expandable from the first internal diameter to the second internal diameter by the inflation of the balloon via the inflation lumen of the catheter body.

The stent device is further used in combination with a pair of retaining sheaths which are extended about the opposed ends of the stent device and the balloon for maintaining the stent device in position thereupon. Also the retaining sheaths may serve to provide a smooth covering over the ends of the stent so as to prevent the ends of the stent from traumatizing the luminal walls of the blood vessel during insertion and advancement of the introducer-mounted stent device. The retaining sheaths are preferably configured and constructed to tear away from the stent as the stent is expanded by the balloon. Thereafter, the partially torn-away retaining sheaths will remain connected to the catheter so as to be extracted and removed along with the deflated balloon and catheter. The retaining sheaths may be formed of any suitable material and may preferably be formed of perforated plastic. The retaining sheaths may be applied by molding, wrapping, forming, heat shrinking, solvent pre-expansion/post-shrinking or any other suitable application method. In embodiments wherein the retaining sheaths are formed of soft pliable elastomeric material such as silicone, polyurethane or latex, such retaining sheaths may be elastically expanded and subsequently allowed to contract in place over top of the ends of the stent device. Alternatively, at least some such elastomeric materials may be initially expanded by solvent swelling and subsequently permitted to post-contract into place over the ends of the stent device.

Further in accordance with the present invention, there is provided a method of inserting a pressure expandable stent into an anatomical passageway which comprises the steps of positioning a stent upon an inflatable balloon while the internal flow channel of the stent is of a first diameter, and inserting the balloon upon which the stent is positioned into the anatomical passageway to a desired treatment site located therewithin. Thereafter, the balloon is inflated to expand the flow channel of the stent from the first internal diameter to a second internal diameter whereby the stent radially engages the anatomical passageway to maintain the patency thereof. The balloon is then deflated to cause the balloon to retract out of contact with the stent, with the balloon subsequently being removed from the anatomical passageway such that stent remains operatively positioned therewithin. The preferred method may further comprise the steps of wrapping the ends of the stent with the sheath material which will tear under pressure when the balloon is inflated, and selecting the size of the stent and the number of convolutions defined thereby such that the expansion of the flow channel to the second internal diameter will cause the stent to radially engage the anatomical passageway in a manner wherein the angle defined between any adjacent pair of the straight segments of the stent separated by one of the radius bends does not exceed 30°.

The preferred method of utilizing the stent may be carried out during an open surgical procedure by passing the balloon having the stent positioned thereupon through an incision which provides access into the anatomical passageway. Alternately, the method may be carried out by percutaneous insertion wherein the balloon having the stent positioned thereupon is passed percutaneously through a tubular introducer and subsequently transluminally advanced into the anatomical passageway. In those instances wherein the anatomical passageway comprises a blood vessel, the treatment site may be an area of atherosclerotic plaque occlusion or a compressed area of the blood vessel. Additionally, the preferred method may be carried out subsequent to a balloon dilation angioplasty procedure which occurs at the treatment site.

BRIEF DESCRIPTION OF THE DRAWINGS

These, as well as other features of the present invention, will become more apparent upon reference to the drawings wherein:

FIG. 1 is a perspective view of the stent device of the present invention as operatively positioned within an anatomical passageway;

FIG. 2a is a side view of the wire member from which the stent is formed;

FIG. 2b is a side elevational view illustrating the manner in which the wire member is bent at spaced locations along the length thereof during the process of fabricating the stent device;

FIG. 2c is a perspective view illustrating the manner in which the opposed ends of the wire member are drawn toward each other subsequent to the bending of the wire member in the manner shown in FIG. 2b;

FIG. 2d is a perspective view of the stent device as formed by the attachment of the opposed ends of the wire member to each other;

FIG. 3a is a partial side elevational view of a wire member having enlarged, bulbous bends formed therein;

FIG. 3b is a partial side-elevational view illustrating the configuration of the wire member shown in FIG. 3a subsequent to the expansion thereof;

FIG. 3c is a partial side-elevational view of a wire member having an enlarged, generally key-shaped bend formed therewithin;

FIG. 3d is a partial side-elevational view illustrating the configuration of the wire member shown in FIG. 3c subsequent to the expansion thereof;

FIG. 4a is an enlarged perspective view of the distal portion of a balloon catheter having the stent device operatively positioned thereupon;

FIG. 4b is an enlarged perspective view of a retaining sheath utilized to maintain the stent device in position upon the balloon of the balloon catheter;

FIG. 4c is an enlarged perspective view of the distal portion of a balloon catheter wherein the balloon is inflated to expand the stent device.

DETAILED DESCRIPTION OF THE PREFERRED EMBODIMENT

Figure 5A:
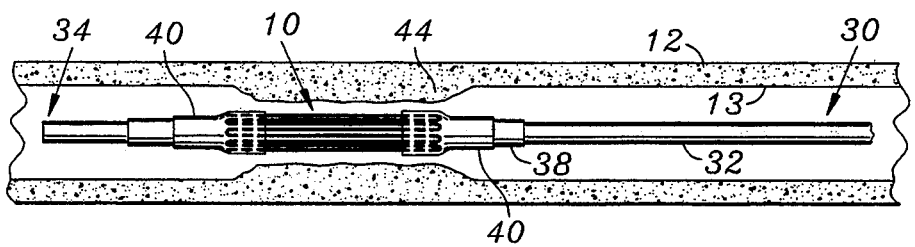
FIGS. 5a–5d are side elevational views illustrating the preferred method of utilizing the stent device of the present invention.
Figure 5B:
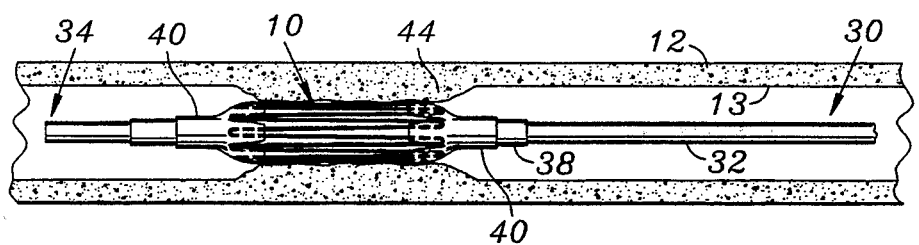
Figure 5C:
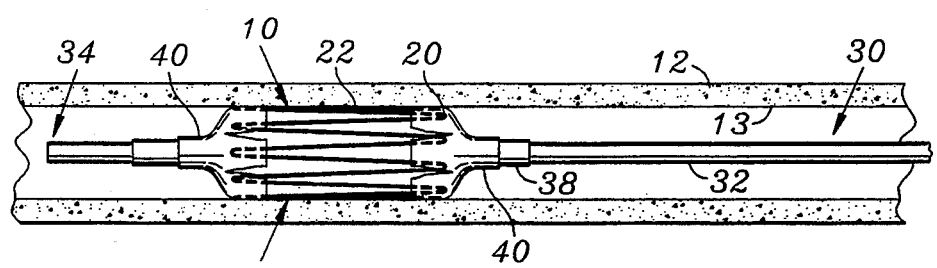

The detailed description set forth below in connection with the appended drawings is intended merely as a description of the presently preferred embodiments of the invention, and is not intended to represent the only form in which the present invention may be constructed or utilized. The description sets forth the functions and sequence of steps for construction and implementation of the invention in connection with the illustrated embodiments. It is to be understood, however, that the same or equivalent functions and sequences may be accomplished by different embodiments that are also intended to be encompassed within the spirit and scope of the invention.

Referring now to FIG. 1, perspectively illustrated is a stent device 10 constructed in accordance with the preferred embodiment of the present invention as operatively positioned within an anatomical passageway 12 such as a blood vessel. As will be discussed in more detail below, the stent 10 may be utilized to reinforce or dilate numerous types of anatomical passageways, including blood vessels, urogenital passageways and bioducts. In relation to cardiovascular applications, the stent 10 is typically inserted into a blood vessel to dilate areas of the vessel which have become occluded by atherosclerotic plaque or constricted by an adjacent tumor.

Referring now to FIGS. 2a-2d, the stent 10 is formed from an elongate wire member 14 defining a first end 16 and a second end 18. The wire member 14 is preferably fabricated from a titanium alloy, though other biocompatible materials of similar resiliency may be utilized as an alternative. The wire member 14 is manipulated in a manner defining a multiplicity of radius bends 20 which are formed at spaced locations along the length thereof. Each of the bends 20 preferably forms an angle of approximately 180° so as to define multiple straight segments 22 of the wire member 14 between the bends 20. As best seen in FIG. 2b, the straight segments 22 defined between the radius bends 20 are disposed in generally parallel, convoluted relation to one another. Due to the formation of the radius bends 20 and straight segments 22, the wire member 14 defines a multiplicity of convolutions 24, each of which are formed by an adjacent pair of straight segments 22 and a single radius bend 20. The wire member 14 shown in FIG. 2b includes eight (8) convolutions formed therein, while the wire member 14 shown in FIG. 2c includes ten (10) convolutions formed therein. In the preferred embodiment, the radius bends 20 are formed in the wire member 14 via the engagement of the wire member 14 to a suitable mandrel, though it will be recognized that other formation techniques may also be utilized.

When the wire member 14 is bent to define the desired number of convolutions 24, the first end 16 of the wire member 14 terminates at approximately the midpoint of the adjacent straight segment 22. Similarly, the second end 18 of the wire member 14 terminates at approximately the midpoint of the straight segment 22 adjacent thereto. The wire member 14 possesses sufficient flexibility so as to allow the first end 16 to be rolled toward the second end 18 in the manner shown in FIG. 2c subsequent to the formation of the convolutions 24 therewithin. As seen in FIG. 2d, the convoluted wire member 14 is rolled so as to position the first end 16 thereof into coaxial alignment with the second end 18. Thereafter, the first end 16 is fused to the second end 18. Such fusion is preferably facilitated via a welding process, though other attachment methods may be utilized. When the first and second ends 16, 18 are properly attached to each other, the straight segments 22 of the wire member 14 assume a generally cylindrical array about a longitudinal axis A and define therewithin an internal flow channel 26 having a first internal diameter D1.

In the preferred embodiment, the stent 10 is adapted to be pressure expandable so as to allow the flow channel 26 to be radially expanded from the first internal diameter D1 to a second internal diameter D2 subsequent to the positioning of the stent 10 at a treatment site within the anatomical passageway 12. When the stent device 10, and more particularly the flow channel 26 thereof, is expanded from the first internal diameter D1 to the second internal diameter D2, the stent 10 is caused to radially engage the inner wall 13 of the anatomical passageway 12 to maintain the patency thereof. The manner in which the stent 10 is expanded will be discussed in more detail below.

Figure 5D:
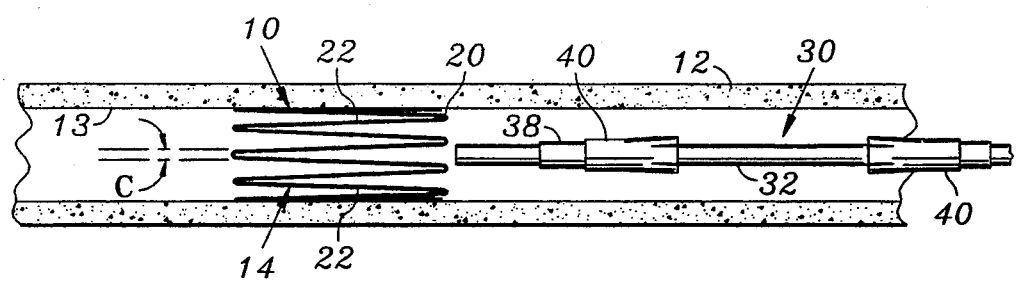

As seen in FIGS. 1 and 5d, the stent 10 is sized such that when the flow channel 26 is expanded to the second internal diameter D2, the angle C defined between any pair of straight segments 22 disposed in side-by-side relation and separated by one of the radius bends 20 does not exceed 45°, and preferably does not exceed 30°. When the flow channel 26 is of the first internal diameter D1 prior to the expansion of the stent 10, each pair of straight segments 22 which are separated by a single radius bend 20 extend in substantially parallel relation to each other, and thus, in substantially parallel relation to the longitudinal axis A of the flow channel 26. However, when the flow channel 26 is radially expanded to the second internal D2, the straight segments 22 of each adjacent pair are necessarily caused to be angularly offset from one another. As will be recognized, the relationship of each adjacent pair of straight segments 22 to the longitudinal axis A of the flow channel 26 is a function of the angle C defined therebetween. In this respect, as the angle C increases, the straight segments 22 of each pair are increasingly disposed out of parallel with the longitudinal axis A. Conversely, as the angle C decreases, the straight segments 22 of each pair are increasingly disposed in parallel relation to the longitudinal axis A.

Importantly, the stent 10 constructed in accordance with the present invention is adapted to facilitate laminar flow through the flow channel 26 thereof when the stent 10 is radially engaged to the inner wall 13 of the anatomical passageway 12. Such laminar flow is achieved by maintaining the relationship between the straight segments 22 and the longitudinal axis A as close to parallel as possible. This substantially parallel relationship between the straight segments 22 and longitudinal axis A is achieved by sizing the stent 10 such that the angle C between each adjacent pair of straight segments 22 does not exceed 30° when the flow channel 26 is radially expanded to the second diameter D2 (i.e., the angle between any single straight segment 22 relative the longitudinal axis A does not exceed 15°).

The size of the stent 10 is a function of the number of convolutions 24 formed therein and total length of the wire member 14. The number of convolutions 24 formed within the stent 10 is selected based on the internal diameter of the anatomical passageway 12 into which the stent 10 is to be operatively positioned. As will be recognized, the larger the internal diameter of the anatomical passageway 12, the greater the stent 10 must be expanded to cause the same to radially engage the inner wall 13 of the anatomical passageway 12. Importantly, as the number of convolutions 24 formed within the stent 10 increases, the diameter D2 to which the flow channel 26 is expandable while maintaining the angle C between each adjacent pair of straight segments 22 at 30° or less also increases. As such, a stent 10 selected for use in an anatomical passageway 12 having a large internal diameter will include more convolutions 24 formed therein than a stent 10 utilized in an anatomical passageway 12 having a smaller internal diameter.

As previously explained, prior to the expansion of the stent 10, the straight segments 22 thereof are disposed in generally parallel relation to each other. When the flow channel 26 is radially expanded from the first internal diameter D1 to the second internal diameter D2, each adjacent pair of straight segments 22 (i.e., those straight segments separated by a single radius bend 20) define the angle C therebetween which preferably does not exceed 30°, thus maintaining the straight segments 22 in substantially parallel relation to the longitudinal axis A of the flow channel 26 and promoting laminar flow therethrough. As will be recognized, such laminar flow would be optimized if the straight segments 22 were each disposed in substantially parallel relation to the longitudinal axis A, even after the flow channel 26 is radially expanded to the second internal diameter D2.

Referring now to FIGS. 3a and 3b, the stent 10 may be formed to include radius bends 20a having an enlarged, bulbous configuration. Advantageously, the formation of the bends 20a in this manner will cause the straight segments 22 to remain in substantially parallel relation to the longitudinal axis A subsequent to the expansion of the flow channel 26 to the second internal diameter D2. To allow the bends 20a to facilitate the transition of the straight segments 22 from the configuration shown in FIG. 3a to that shown in FIG. 3b, the wire member 14 is formed to include weakened portions 28 which are defined between each of the bends 20a and the pair of straight segments 22 separated thereby. When the flow channel 26 of the stent 10 is expanded from the first diameter D1 to the second diameter D2, the weakened portions 28 act in concert with the bends 20a to maintain the straight segments 22 in substantially parallel relation to the longitudinal axis A of the flow channel 26, thus facilitating laminar flow therethrough.

Referring now to FIGS. 3c and 3d, as an alternative to the enlarged, bulbous bends 20a, the stent 20 may be formed to include enlarged, generally key-shaped bends 20b which, like the bends 20a, are also adapted to facilitate the positioning of the straight segments 22 in substantially parallel relation to the longitudinal axis A subsequent to the expansion of the stent 10. As such, to facilitate the expansion of the straight segments 22 from the configuration shown in FIG. 3c to that shown in FIG. 3d, the wire member 14, in addition to including the bends 20b, also includes the weakened portions 28 defined between each bend 20b and the adjacent straight segments 22 separated thereby.

Referring now to FIG. 4a, since the stent 10 is not self-expanding, but rather is pressure expandable, the stent 10 is preferably utilized in conjunction with a balloon catheter 30 which facilitates the expansion of the stent 10 from the first internal diameter D1 to the second internal diameter D2. The balloon catheter 30 generally comprises an elongate catheter body 32 defining an open distal end 34 and a hollow lumen 36 extending longitudinally therethrough. Positioned upon the outer surface of the catheter body 32 adjacent the distal end 34 thereof is a dilation balloon 38, the opposed ends of which are attached to the outer surface of the catheter body 32, typically via a heat sealing process. Although not shown, the catheter body 32 defines a balloon inflation lumen which is in fluid communication with the inflation space defined between the balloon 38 and the outer surface of the catheter body 32 for selectively inflating and deflating the balloon 38. However, it will be recognized that the catheter body 32 may be formed with a closed distal end 34, and that the lumen 36 may function as the balloon inflation lumen.

In an alternative construction, the dilation balloon 38 may comprise an integral portion of the catheter body sized and located so as to effect the intended placement and expansion of the stent 10 of the present invention.

In the preferred embodiment, the stent 10 is extended over the catheter body 32 when the internal flow channel 26 is of the first internal diameter D1 such that the balloon 38 is centrally disposed within the flow channel 26. As will be described in more detail below, due to the positioning of the balloon 38 within the flow channel 26, the inflation of the balloon 38 facilitates the radial expansion of the flow channel 26 from the first internal diameter D1 to the second internal diameter D2.

The stent 10 is preferably maintained in position upon the dilation balloon 38 via a pair of tubular retaining sheaths 40, each of which are extended about one of the opposed ends of the stent 10 and an end portion of the balloon 38. As best seen in FIG. 4b, each of the retaining sheaths 40 has a generally cylindrical configuration and is provided with sets of perforations 42 which extend longitudinally from one end of the sheath 40 to the approximate mid-point thereof. As seen in FIG. 4a, the retaining sheaths 40 are interfaced to the stent 10 and dilation balloon 38 such that the portions thereof including the perforations 42 disposed therein are extended over (i.e., overlap) the ends of the stent 10, with the non-perforated portions being directly engaged to the outer surface of the balloon 38. The retaining sheaths 40 are preferably formed of plastic which is weakened or perforated such that the retaining sheaths 40 will tear away from the ends of the stent 10 as the stent 10 is expanded by the balloon 38.

The retaining sheaths 40 may be formed of any suitable material. In some embodiments, the retaining sheaths 40 may be formed of heat shrinkable plastic material and such retaining sheaths 40 may be heat shrunk into place on the ends of the stent 10. In alternative embodiments, the retaining sheaths 40 may be formed of soft pliable elastomeric material such as silicone polyurethane or latex, although such materials may not be heat shrinkable. In such embodiments, the elastomeric materials may be elastically expanded and allowed to elastically contract into place on the ends of the stent 10 or, alternatively, may be initially swelled by solvent application and subsequently allowed to post-contract about the outer surface of the catheter body and over the ends of the stent 10, as shown.

As seen in FIG. 4c, when the balloon 38 having the stent 10 positioned thereabout is inflated, the retaining sheaths 40 are adapted to tear under pressure as the stent 10 is radially expanded, thus releasing the stent 10 from engagement to the balloon 38. As will be recognized, due to the inclusion of the perforations 42 within the retaining sheaths 40, only those portions which are extended over the opposed ends of the stent 10 are torn by the expansion of the balloon 38, thus preventing the retaining sheaths 40 from becoming dislodged from the balloon 38 and remaining in the anatomical passageway 12 subsequent to the removal of the balloon catheter 30 from therewithin. Importantly, when the stent 10 is fully radially expanded into engagement with the inner wall 13, the torn ends of the retaining sheaths 40 are not captured between the expanded stent 10 and the inner wall 13. As such, subsequent to the deflation of the balloon 38, the catheter body 32, balloon 38 and torn retaining sheaths 40 may easily be pulled proximally through and out of the internal flow channel 26 of the stent 10, thus leaving the stent 10 operatively positioned at the treatment site within the anatomical passageway 12.

Referring now to FIGS. 5a-5d, the stent 10 of the present invention is utilized by initially positioning the same upon the balloon 38 of the balloon catheter 30 while the internal flow channel 26 is of the first internal diameter D1. The ends of the stent 10 are then wrapped by the retaining sheaths 40 in the aforementioned manner to maintain the stent 10 in position upon the balloon 38. Thereafter, the balloon catheter 30 upon which the stent 10 is positioned is transluminally advanced through the anatomical passageway 12 to a desired treatment site, such as one including an atherosclerotic plaque occlusion 44. After the positioning of the balloon 38 at the treatment site, the balloon 38 is inflated via the inflation lumen, thus expanding the internal flow channel 26 from the first internal diameter D1 to the second internal diameter D2, which in turn causes the stent 10 to radially engage the inner wall 13 of the anatomical passageway 12 to maintain the patency thereof. As previously explained, the inflation of the balloon 38 causes the retaining sheaths 40 to tear, thus releasing the stent 10 from engagement to the balloon 38. The balloon 38 is then deflated, with the balloon catheter 30 being removed from within the anatomical passageway 12 such that the stent 10 remains operatively positioned at the occlusion 44 therewithin.

The preferred method of the present invention may be carried out during an open surgical procedure wherein the balloon catheter 30 having the stent 10 positioned thereupon is initially passed through an incision which provides access into the anatomical passageway 12. The method may alternately be carried out by percutaneous insertion wherein the balloon catheter 30 having the stent 10 positioned thereupon is passed percutaneously through a tubular introducer and subsequently transluminally advanced into the anatomical passageway 12 to the occlusion 44 therewithin. When the anatomical passageway 12 in which the stent 10 is utilized comprises a blood vessel, the treatment site typically is an area of atherosclerotic plaque occlusion or a compressed area of the blood vessel which has been affected by a tumor or other pathology. Additionally, the present method is typically carried out subsequent to a balloon dilation angioplasty, or any other type of angioplasty procedure at the treatment site.

Prior to the positioning of the stent 10 upon the balloon 38 of the balloon catheter 30, the size of the stent 10, and more particularly the number of convolutions 24 defined thereby, is selected such that the angle C defined between any adjacent pair of the straight segments 22 does not exceed 30° when the stent 10 radially engages the inner wall 13 of the anatomical passageway 12. Once again, limiting the maximum angular displacement between each pair of straight segments 22 to 30° or less facilitates laminar flow through the flow channel 26 when the stent 10 is operatively positioned within the anatomical passageway 12.

Although the invention has been described herein with specific reference to presently preferred embodiments thereof, it will be appreciated by those skilled in the art that various additions, modifications, deletions and alterations may be made to such preferred embodiments without departing from the spirit and scope of the invention. Accordingly, it is intended that all reasonably foreseeable additions, deletions, alterations and modifications be included within the scope of the invention as defined in the following claims.

What is claimed is:

1. A pressure expandable stent device having a first internal diameter (D1) and subsequently expandable to a second internal diameter (D2), said stent device comprising:

an elongate wire member having first and second ends;

a multiplicity of radius bends formed at spaced locations along said wire member, each of said bends forming an angle of approximately 180° so as to define therebetween multiple straight segments of said wire member disposed in generally parallel, convoluted relation to one another;

said first and second ends of said wire member being positioned in co-axial alignment and fused to one another;

said straight segments of said wire member thereby assuming a cylindrical array about a longitudinal axis and defining therewithin an internal flow channel of said first internal diameter (D1);

said stent device being radially expandable to a configuration wherein said internal flow channel is of said second internal diameter (D2); and each of said radius bends having an enlarged, bulbous configuration and said wire member being formed to include weakened portions which are defined between each of said radius bends and the pair of straight segments separated thereby, said bulbous radius bends and said weakened portions being adapted to maintain said straight segments in substantially parallel relation when the stent device is expanded from the first internal diameter (D1) to the second internal diameter (D2).

2. The stent device of claim 1 wherein the angle defined between any pair of said straight segments which are disposed in side-by-side relation and separated by one of said bends does not exceed 45° when the flow channel is expanded to the second internal diameter.

3. The stent device of claim 1 wherein the angle defined between any pair of said straight segments which are disposed in side-by-side relation and separated by one of said bends does not exceed 30° when the flow channel is expanded to the second internal diameter.

4. The stent device of claim 1 wherein the first and second ends of said wire member are attached to each other via a weld.

5. The stent device of claim 1 wherein said wire member is fabricated from a titanium alloy.

6. The stent device of claim 1 further in combination with a balloon catheter comprising a catheter body, an inflatable balloon positioned upon said catheter body and an inflation lumen defined within said catheter body for selectively inflating and deflating said balloon, said stent device being extended over said catheter body to a position whereat said balloon is disposed within said flow channel, and radially expandable from the first internal diameter to the second internal diameter by the inflation of said balloon via said inflation lumen.

7. The stent device of claim 6 further in combination with at least one retaining sheath which is extended about one end of said stent device and said catheter body for maintaining said stent device in position upon said balloon, said sheath being adapted to tear under pressure, thus releasing the stent device from engagement to the balloon catheter when the balloon is inflated and the stent device expanded from the first internal diameter to the second internal diameter.

8. The stent device of claim 7 wherein a pair of retaining sheaths are extended about the opposed ends of the stent device and portions of the balloon.

9. The stent device of claim 8 wherein said retaining sheaths are each formed of perforated plastic which is shrunk about the ends of the stent device and portions of the balloon.

10. The stent device of claim 8 wherein said retaining sheaths are each formed of elastomeric material.

11. A pressure expandable stent device having a first internal diameter (D1) and subsequently expandable to a second internal diameter (D2), said stent device comprising:

an elongate wire member having first and second ends;

a multiplicity of radius bends formed at spaced locations along said wire member, each of said bends forming an angle of approximately 180° so as to define therebetween multiple straight segments of said wire member disposed in generally parallel, convoluted relation to one another;

said first and second ends of said wire member being positioned in co-axial alignment and fused to one another;

said straight segments of said wire member thereby assuming a cylindrical array about a longitudinal axis and defining therewithin an internal flow channel of said first internal diameter (D1);

said stent device being radially expandable to a configuration wherein said internal flow channel is of said second internal diameter (D2); and each of said radius bends having an enlarged, generally key-shaped configuration and said wire member being formed to include weakened portions which are defined between each of said radius bends and the pair of straight segments separated thereby, said key-shaped radius bends and said weakened portions being adapted to maintain said straight segments in substantially parallel relation when the stent device is expanded from the first internal diameter (D1) to the second internal diameter (D2).

12. The stent device of claim 11 wherein the angle defined between any pair of said straight segments which are disposed in side-by-side relation and separated by one of said bends does not exceed 45° when the flow channel is expanded to the second internal diameter.

13. The stent device of claim 11 wherein the angle defined between any pair of said straight segments which are disposed in side-by-side relation and separated by one of said bends does not exceed 30° when the flow channel is expanded to the second internal diameter.

14. The stent device of claim 11 wherein the first and second ends of said wire member are attached to each other via a weld.

15. The stent device of claim 11 wherein said wire member is fabricated from a titanium alloy.

16. The stent device of claim 11 further in combination with a balloon catheter comprising a catheter body, an inflatable balloon positioned upon said catheter body and an inflation lumen defined within said catheter body for selectively inflating and deflating said balloon, said stent device being extended over said catheter body to a position whereat said balloon is disposed within said flow channel, and radially expandable from the first internal diameter to the second internal diameter by the inflation of said balloon via said inflation lumen.

17. The stent device of claim 16 further in combination with at least one retaining sheath which is extended about one end of said stent device and said catheter body for maintaining said stent device in position upon said balloon, said sheath being adapted to tear under pressure, thus releasing the stent device from engagement to the balloon catheter when the balloon is inflated and the stent device expanded from the first internal diameter to the second internal diameter.

18. The stent device of claim 17 wherein a pair of retaining sheaths are extended about the opposed ends of the stent device and portions of the balloon.

19. The stent device of claim 18 wherein said retaining sheaths are each formed of perforated plastic which is shrunk about the ends of the stent device and portions of the balloon.

20. The stent device of claim 18 wherein said retaining sheaths are each formed of elastomeric material.

21. A pressure expandable stent device having a first internal diameter (D1) and subsequently expandable to a second internal diameter (D2), said stent device comprising:

an elongate wire member having first and second ends;

a multiplicity of radius bends formed at spaced locations along said wire member, each of said bends forming an angle of approximately 180° so as to define therebetween multiple straight segments of said wire member disposed in generally parallel, convoluted relation to one another;

said first and second ends of said wire member being positioned in co-axial alignment and fused to one another;

said straight segments of said wire member thereby assuming a cylindrical array about a longitudinal axis and defining therewith an internal flow channel of said first internal diameter (D1); and said stent device being radially expandable to a configuration wherein said internal flow channel is of said second internal diameter (D2);

said stent device being used in combination with a balloon catheter comprising an catheter body, an inflatable balloon positioned upon said catheter body and an inflation lumen defined within said catheter body for selectively inflating and deflating said balloon, said stent device being extended over said catheter body to a position whereat said balloon is disposed within said flow channel, and radially expandable from the first internal diameter (D1) to the second internal diameter (D2) by the inflation of said balloon via said inflation lumen;

said stent device being maintained in position upon said balloon by a pair of retaining sheaths which are extended about the opposed ends of the stent device and portions of the balloon, said retaining sheaths being adapted to tear under pressure, thus releasing the stent device from engagement to the balloon catheter when the balloon is inflated and the stent device expanded from the first internal diameter (D1) to the second internal diameter (D2);

said retaining sheaths each being formed of perforated plastic which is shrunk about the ends of the stent device and portions of the balloon.

22. The stent device of claim 21 wherein the angle defined between any pair of said straight segments which are disposed in side-by-side relation and separated by one of said bends does not exceed 45° when the flow channel is expanded to the second internal diameter.

23. The stent device of claim 21 wherein the angle defined between any pair of said straight segments which are disposed in side-by-side relation and separated by one of said bends does not exceed 30° when the flow channel is expanded to the second internal diameter.

24. The stent device of claim 21 wherein the first and second ends of said wire member are attached to each other via a weld.

25. The stent device of claim 21 wherein said wire member is fabricated from a titanium alloy.

26. The stent device of claim 21 wherein each of said radius bends has an enlarged, bulbous configuration and said wire member is formed to include weakened portions which are defined between each of said radius bends and the pair of straight segments separated thereby, said bulbous radius bends and said weakened portions being adapted to maintain said straight segments in substantially parallel relation when the stent device is expanded from the first internal diameter to the second internal diameter.

27. The stent device of claim 21 wherein each of said radius bends has an enlarged, generally key-shaped configuration and said wire member is formed to include weakened portions which are defined between each of said radius bends and the pair of straight segments separated thereby, said key-shaped radius bends and said weakened portions being adapted to maintain said straight segments in substantially parallel relation when the stent device is expanded from the first internal diameter to the second internal diameter.

28. The stent device of claim 21 wherein said retaining sheaths are each formed of elastomeric material.

29. A method of inserting a pressure expandable stent into an anatomical passageway, comprising the steps of:
   a) providing a stent which comprises:
      and elongate wire member having first and second ends; and
      a multiplicity of radius bends formed at spaced locations along said wire member so as to define therebetween multiple straight segments of said wire disposed in generally parallel, convoluted relation to one another;
      said first and second ends being attached to each other in a manner causing said straight segments to assume a cylindrical array defining therewithin an internal flow channel of a first internal diameter, with said stent device being expandable to a configuration wherein said flow channel is of a second internal diameter;
      the size of the stent and the number of convolutions defined thereby being selected such that the expansion of the flow channel to the second internal diameter causes the stent to radially engage the anatomical passageway in a manner wherein the angel defined between any pair of said straight segments which are disposed in side-by-side relation and separated by one of said bends does not exceed 30°;
   b) positioning said stent upon an inflatable balloon while the internal flow channel is of the first internal diameter;
   c) inserting the balloon upon which the stent is positioned into said anatomical passageway to a desired treatment cite located therewithin;
   d) inflating said balloon to expand said flow channel from said first internal diameter to said second internal diameter whereby said stent radially engages said anatomical passageway to maintain the patency thereof;
   e) deflating said balloon to retract the balloon out of contact with said stent; and
   f) removing the balloon from the anatomical passageway such that the stent remains operatively positioned therewithin.

30. The method of claim 29 wherein step b) further comprises the step of wrapping the ends of the stent with the sheath material which will tear under pressure when the balloon is inflated, and step d) further comprises the step of causing the sheath material to tear as the balloon is inflated.

31. The method of claim 29 wherein said method is carried out during an open surgical procedure and step b) further comprises the step of passing the balloon having the stent positioned thereupon through an incision which provides access into the anatomical passageway.

32. The method of claim 29 wherein said method is carried out by percutaneous insertion and step b) further comprises the step of passing the balloon having the stent positioned thereupon percutaneously through a tubular introducer and subsequently transluminally advancing said balloon into said anatomical passageway.

33. The method of claim 29 wherein said anatomical passageway comprises a blood vessel.

34. The method of claim 33 wherein said treatment site is an area of atherosclerotic plaque occlusion.

35. The method of claim 33 wherein said treatment site is a compressed area of said blood vessel.

36. The method of claim 29 wherein said method is carried out subsequent to an angioplasty at the treatment site.

37. The method of claim 36 wherein said method is carried out subsequent to a balloon dilation angioplasty at the treatment site.

38. The method of claim 36 wherein said method is carried out subsequent to an atherectomy procedure at the treatment site.

39. The method of claim 36 wherein said method is carried out subsequent to an ultrasonic ablation procedure at the treatment site.

40. The method of claim 36 wherein said method is carried out subsequent to a laser ablative procedure at the treatment site.

41. A method of inserting a pressure expandable stent into an anatomical passageway, comprising the steps of:
   a) providing a stent which comprises:
      an elongate wire member having first and second ends; and
      a multiplicity of bends formed at spaced locations along said wire member so as to define therebetween multiple straight segments of said wire disposed in generally parallel, convoluted relation to one another;
      said first and second ends being attached to each other in a manner causing said straight segments to assume a cylindrical array defining therewithin an internal flow channel of a first internal diameter, with said stent device being expandable to a configuration wherein said flow channel is of a second internal diameter;
   b) positioning said stent upon an inflatable balloon while the internal flow channel is of the first internal diameter;
   c) inserting the balloon upon which the stent is positioned into said anatomical passageway to a desired treatment site located therewithin;
   d) inflating said balloon to expand said flow channel from said first internal diameter to said second internal diameter whereby said stent radially engages said anatomical passageway to maintain the patency thereof;

e) deflating said balloon to retract the balloon out of contact with said stent; and f) removing the balloon from the anatomical passageway such that the stent remains operatively positioned therewithin;

said method being carried out subsequent to an ultrasonic ablation procedure at the treatment site.

42. The method of claim 41 wherein step b) further comprises the step of wrapping the ends of the stent with the sheath material which will tear under pressure when the balloon is inflated, and step d) further comprises the step of causing the sheath material to tear as the balloon is inflated.

43. The method of claim 41 wherein step a) further comprises the step of selecting the size of the stent and the number of convolutions defined thereby such that the expansion of the flow channel to the second internal diameter causes the stent to radially engage the anatomical passageway in a manner wherein the angle defined between any pair of said straight segments which are disposed in side-by-side relation and separated by one of said bends does not exceed 30°.

44. The method of claim 41 wherein said method is carried out during an open surgical procedure and step b) further comprises the step of passing the balloon having the stent positioned thereupon through an incision which provides access into the anatomical passageway.

45. The method of claim 41 wherein said method is carried out by percutaneous insertion and step b) further comprises the step of passing the balloon having the stent positioned thereupon percutaneously through a tubular introducer and subsequently transluminally advancing said balloon into said anatomical passageway.

46. The method of claim 41 wherein said anatomical passageway comprises a blood vessel.

47. The method of claim 46 wherein said treatment site is an area of atherosclerotic plaque occlusion.

48. A method of inserting a pressure expandable stent into an anatomical passageway, comprising the steps of:

a) providing a stent which comprises:
an elongate wire member having first and second ends; and
a multiplicity of radius bends formed at spaced locations along said wire member so as to define therebetween multiple straight segments of said wire disposed in generally parallel, convoluted relation to one another;
said first and second ends being attached to each other in a manner causing said straight segments to assume a cylindrical array defining therewithin an internal flow channel of a first internal diameter, with said stent device being expandable to a configuration wherein said flow channel is of a second internal diameter;

b) positioning said stent upon an inflatable balloon while the internal flow channel is of the first internal diameter;

c) inserting the balloon upon which the stent is positioned into said anatomical passageway to a desired treatment site located therewithin;

d) inflating said balloon to expand said flow channel from said first internal diameter to said second internal diameter whereby said stent radially engages said anatomical passageway to maintain the patency thereof;

e) deflating said balloon to retract the balloon out of contact with said stent; and f) removing the balloon from the anatomical passageway such that the stent remains operatively positioned therewithin;

said method being carried out subsequent to a laser ablative procedure at the treatment site.

49. The method of claim 48 wherein step b) further comprises the step of wrapping the ends of the stent with the sheath material which will tear under pressure when the balloon is inflated, and step d) further comprises the step of causing the sheath material to tear as the balloon is inflated.

50. The method of claim 48 wherein step a) further comprises the step of selecting the size of the stent and the number of convolutions defined thereby such that the expansion of the flow channel to the second internal diameter causes the stent to radially engage the anatomical passageway in a manner wherein the angle defined between any pair of said straight segments which are disposed in side-by-side relation and separated by one of said bends does not exceed 30°.

51. The method of claim 48 wherein said method is carried out during an open surgical procedure and step b) further comprises the step of passing the balloon having the stent positioned thereupon through an incision which provides access into the anatomical passageway.

52. The method of claim 48 wherein said method is carried out by percutaneous insertion and step b) further comprises the step of passing the balloon having the stent positioned thereupon percutaneously through a tubular introducer and subsequently transluminally advancing said balloon into said anatomical passageway.

53. The method of claim 48 wherein said anatomical passageway comprises a blood vessel.

54. The method of claim 53 wherein said treatment site is an area of atherosclerotic plaque occlusion.

* * * * *